United States Patent [19]

Fried

[11] 3,979,458

[45] Sept. 7, 1976

[54] PRODUCTION OF UNSATURATED CARBOCYCLIC KETONES

[75] Inventor: John H. Fried, Palo Alto, Calif.

[73] Assignee: Syntex Corporation, Panama, Panama

[22] Filed: Jan. 10, 1975

[21] Appl. No.: 540,015

Related U.S. Application Data

[60] Division of Ser. No. 747,465, July 25, 1968, Pat. No. 3,880,884, which is a continuation-in-part of Ser. No. 687,502, Dec. 4, 1967, Pat. No. 3,639,428.

[52] U.S. Cl. .............................................. 260/586 E
[51] Int. Cl.² ........................................... C07C 49/00
[58] Field of Search ................................. 260/586 E

[56] References Cited

UNITED STATES PATENTS

| | | | |
|---|---|---|---|
| 3,019,252 | 1/1962 | Nomine et al. | 260/476 |
| 3,117,979 | 1/1964 | Nomine et al. | 260/340.9 |
| 3,312,717 | 4/1967 | Baran | 260/343.2 |
| 3,361,770 | 1/1968 | Romeo | 260/347.8 |
| 3,413,314 | 11/1968 | Amiard et al. | 260/343.2 |
| 3,431,191 | 3/1969 | Anner et al. | 260/586 E |
| 3,446,849 | 5/1969 | Los | 260/586 H |
| 3,459,791 | 8/1969 | Anner et al. | 260/488 |
| 3,574,688 | 4/1971 | Bucourt et al. | 260/343.2 |
| 3,644,429 | 2/1972 | Hajos et al. | 260/345.9 |
| 3,704,324 | 11/1972 | Uskokovic | 260/586 H |
| 3,897,460 | 7/1975 | Hajos | 260/340.9 |

*Primary Examiner*—Gerald A. Schwartz
*Attorney, Agent, or Firm*—Lawrence S. Squires; William B. Walker

[57] ABSTRACT

Preparation of $\alpha,\beta$-unsaturated carbocyclic ketones by reacting an enol lactone with a carbanion generated by treatment of a methylphosphonate or a monosubstituted methylphosphonate with base.

1 Claim, No Drawings

PRODUCTION OF UNSATURATED CARBOCYCLIC KETONES

This application is a division of U.S. Ser. No. 747,465, filed July 25, 1968, now U.S. Pat. No. 3,880,884, which in turn is a continuation-in-part of U.S. Ser. No. 687,502, filed Dec. 4, 1967, now U.S. Pat. No. 3,639,428.

The present invention relates to the production of unsaturated carbocyclic ketones.

More particularly, this invention relates to a novel process which has general utility for the conversion of enol lactones into α,β-unsaturated carbocyclic ketones.

The expression "enol lactone", as used herein, refers to an unsaturated lactone having α,β-ethylenic unsaturation in respect to the heterocyclic oxygen atom. The expression "α,β-unsaturated carbocyclic ketone", as used herein, refers to a carbocyclic ketone having α,β-ethylenic unsaturation in respect to the keto group.

Prior to the present invention, enol lactones were converted into α,β-unsaturated carbocyclic ketones by a two-step process which involved reacting the enol lactone with about one equivalent of a Grignard reagent, for example, methyl-magnesium chloride, to open the lactone ring and thereafter the thus-obtained diketonic intermediate product was cyclized by treatment with acid or alkali to obtain the carbocyclic ketone. See, for example, U.S. Pat. Nos. 3,057,907 and 3,321,489 and French Pat. No. 1,359,675. In addition to the disadvantage that the conversion of enol lactones into carbocyclic ketones requires at least two steps, prior methods are often difficult to control, unsuitable for 5-membered ring systems, and of very narrow utility in that the α,β-unsaturated carbocyclic ketones obtainable are very limited.

A primary object of the present invention, therefore, is to provide a process for the production of α,β-unsaturated carbocyclic ketones from enol lactones which overcomes the aforementioned disadvantages. Another object of the present invention is to provide a process for the production of α,β-unsaturated carbocyclic ketones which is economical and simple to operate but yet of great flexibility or adaptability in respect to the type of α,β-unsaturated carbocyclic ketone that can be produced. Another object of this invention is to provide a single-step process for the production of α,β-unsaturated carbocyclic ketones. Still another object of the present invention is to provide a process for the production of α,β-unsaturated carbocyclic ketones which is useful in the total synthesis of steroids and to novel intermediates therefor. Other objects, advantages and meritorious features of the present invention will become apparent as the invention is described in more detail hereinafter.

In accordance with the foregoing objects of the present invention, there has been discovered a very versatile process for the production of α,β-unsaturated carbocyclic ketones which comprises reacting, under substantially anhydrous conditions in an organic solvent inert to the reaction, an enol lactone with a carbanion generated by the reaction of base with a phosphonate selected from the group consisting of methylphosphonates and mono-substituted methylphosphonates.

The process of the present invention is applicable to the conversion of enol lactones into α,β-unsaturated carbocyclic ketones in general. The enol lactone can be either a monocyclic enol lactone or a polycyclic compound such as bicyclic, tricyclic and tetracyclic enol lactones depending upon the α,β-unsaturated carbocyclic ketone desired to be obtained. The process of the present invention is particularly suitable for enol lactone starting materials wherein the heterocyclic ring thereof contains at least 5 members and mono-ethylenic unsaturation. The enol lactones which can be converted into α,β-unsaturated carbocyclic ketones by the process of this invention are too numerous to list. Exemplary of the monocyclic and polycyclic enol lactones which can be used in the process of the present invention are α-angelica lactone, Δ⁴-valeryl lactone, isocoumarin, 3-methyl-6,8-dimethoxyisocoumarin, 3-phenylisocoumarin, 3-benzoyl-7,8-dimethoxyisocoumarin, 3-chloroisocoumarin, benzal phthalide, 5,6,7-trimethoxyisocoumarin, δ-lactone of 1β-hydroxy-2β-methyl-2α-(2'-carboxyethyl)-3-hydroxycyclopent-3-ene, δ-lactone of 1β-hydroxy-4-(2'-carboxyethyl)-5-hydroxy-7aβ-methyl-3aα,4β, 7,7a-tetrahydroindane, 4-oxa-17β-acetoxyandrost-5-en-3-one, 3-ethoxy-17-oxa-D-homoestra-1,3,5(10),15-tetraen-17-one, 4-oxa-cholest-5-en-3-one, 17,20;20,21-bismethylenedioxy-4-oxa-11β-hydroxypregn-5-en-3-one, and 3-methoxy-16-oxaestra-1,3,5(10),8, 14-pentaen-17-one.

The phosphonates which are useful in the production of α,β-unsaturated carbocyclic ketones in accordance with the process of the present invention are the methylphosphonates and mono-substituted methylphosphonates. Methylphosphonates and mono-substituted methylphosphonates useful in the present invention are illustrated by the following formulas A and B, respectively:

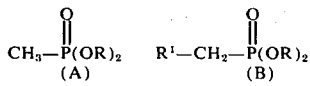

wherein R is selected from the group consisting of substituted and unsubstituted, saturated and unsaturated, aliphatic, carbocyclic and carbocyclic-aliphatic radicals and R¹ is selected from the group consisting of substituted and unsubstituted, saturated and unsaturated, aliphatic, carbocyclic and carbocyclic-aliphatic radicals.

Phosphonates of formulas A and B above can be prepared, for example, by the reaction of a di-substituted phosphite (C) with an organic halide or sulfonate of the formula D and E, respectively, in the presence of a base, e.g. sodium hydride,

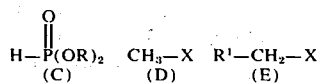

In the above formulas, R and R¹ are as defined above and X is chloro or bromo or $OSO_2R_1$, wherein R is alkyl or aryl. The formation of the phosphonates can be carried out in inert solvents such as ether, tetrahydrofuran, monoglyme, diglyme, or dioxane and preferably in an oxygen-free atmosphere. The method of preparing the phosphonates is not part of the present invention. A suitable procedure for the formation of methylphosphonates and mono-substituted methylphosphonates useful in the present invention is to react a di-substituted phosphite of formula C with an organic halide or sulfonate of formulas D and E in an inert solvent in the presence of about one equivalent of a base such as sodium hydride under an inert atmosphere at a temperature of about −10°C to about room temperature. Other methods are described in, for example, U.S. Pat. No. 2,754,319.

about room temperature. Other methods are described in, for example, U.S. Pat. No. 2,754,319.

While the methylphosphonates and mono-substituted methylphonates which can be employed in the process of the present invention are too numerous to list here, they can be exemplified by the following:

dimethyl methylphosphonate
dimethyl ethylphosphonate
diethyl benzylphosphonate
diethyl methylphosphonate
dicyclohexyl methylphosphonate
diphenyl methylphosphonate
di-(n-butyl) methylphosphonate
dibenzyl methylphosphonate
diethyl methylphosphonate
diethyl 4,4-dimethoxybutylphosphonate
diethyl 4,4-ethylenedioxypentylphosphonate
dimethyl 4,4-dimethoxy-3-methylbut-2-enylphosphonate
diethyl 4-chloropent-3-enylphosphonate
diethyl 4-(tetrahydropyran-2'-yloxy)-pentylphosphonate
diethyl 4,4-ethylenedioxy-3-methylpentylphosphonate
di(methoxyethyl) methylphosphonate
di(2-ethylhexyl) methylphosphonate
di(n-octyl) ethylphosphonate
di(ethoxyethyl) methylphosphonate In the practice of the process of the present invention, a phosphonate of formula A or B is reacted with a base to generate the corresponding carbanion of the formulas A' and B', respectively:

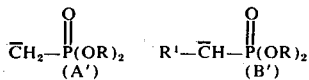

Because of the general instability of the phosphonate carbanion, it is necessary that the reaction between the phosphonate and base be carried out at low temperatures of the order of about −150° to about −20°C, preferably about −100° to about −40°C. After formation of the carbanion is complete, the low temperature of the reaction mixture is maintained during the addition of the enol lactone and thereafter the cooling means removed or otherwise raising the reaction temperature to about room temperature. Suitable bases for generating the carbanion include organo alkali metal compounds such as n-butyl lithium, phenyl lithium, methyl sodium, sodium acetylide, methyl potassium, methyl lithium, tolyl lithium, methyl potassium lithium pyridide, and the like; alkali metal hydrides such as sodium hydride, potassium hydride or lithium hydride; alkali metal amides such as sodamide, and the like.

In practicing the conversion of an enol lactone into the corresponding α,β-unsaturated carbocyclic ketone in accordance with the process of the present invention, the reaction is carried out using about equal molar amounts of the phosphonate, base and enol lactone. More than one molar equivalent of the phosphonate and base can be used but it is generally disadvantageous to do so because the excess reagent may react further with the carbonyl group of the desired carbocyclic ketone. Thus, it is preferred to use about one molar equivalent of the phosphonate and base or a modest excess of each such as up to about 1.2 molar equivalents. Any organic solvent can be used for the reaction medium so long as it is inert to the reaction and liquid at the reaction temperature being used. Suitable organic solvents include ether, tetrahydrofuran, dioxane, monoglyme, diglyme, and the like. The reaction between the carbanion and enol lactone generally goes to completion in from about 0.5 hours to about 48 hours depending upon such factors as temperature and the relative reactivity of the carbanion and the enol lactone. The reaction temperature can vary from about −150°C to about room temperature, preferably about −100°C to about room temperature depending upon such factors as the stability of the carbanion, the relative reactivity of carbanion and enol lactone being reacted and the time in which it is desired to complete the reaction. After formation of the carbanion is complete and the enol lactone has been introduced, the reaction mixture can be permitted to rise to about room temperature in order to complete the reaction in a shorter period of time. Depending upon the stability of the particular carbanion being used, the reaction mixture can be heated above room temperature, for example reflux temperature, if still shorter reaction times are desired. However, because of the general instability of the carbanion, the reaction between the phosphonate and base must be carried out at low temperatures of the order of about −150° to −20°C. For optimum results, it is important that the reaction be conducted under as near anhydrous conditions as possible and preferably under an inert oxygen-free atmosphere such as nitrogen, argon, and the like. While the concentration of the enol lactone and carbanion does not appear to be critical, it is preferred to operate at low concentrations of the order of about two to about twenty-five percent by weight of the reaction medium. The foregoing reaction conditions are largely dependent upon the particular phosphonate, base and enol lactone employed and are presented as a guide. Provided with the foregoing and the examples hereinafter, the most advantageous or optimum conditions and proportions of the enol lactone, phosphonate and base for a particular α,β-unsaturated carbocyclic ketone are easily determinable by one of ordinary skill in the art using routine experimentation.

In the case of enol lactone starting materials having other carbonyl groups present, e.g. an isolated keto group, it is preferable to introduce a protecting group prior to the reaction. In general, the phosphonate anions tend to react faster with the enol lactone group. An isolated keto group can be protected as through formation of the corresponding lower alkylenedioxy or ketal and the keto group regenerated by treatment with acid following completion of the reaction of the enol lactone and phosphonate anion. Alternatively, an isolated keto group can be reduced to the free hydroxyl by the use of reducing agents such as lithium hydride, lithium tri(t-butoxy)aluminum hydride or sodium borohydride and subsequently oxidized using, e.g. chromium trioxide or Jones reagent following completion of the reaction. If a free hydroxyl group is present, there may be some reaction of the hydroxy group with the carbanion and hence require that an excess of the carbanion be used. It is preferred to protect hydroxyl groups by esterification to a carboxylic ester such as acetate, benzoate, cyclopentylpropionate, mesitoate, and the like, or by etherification. Since the ester group in some cases will react with the carbanion to some extent, it is preferred to convert free hydroxyls of the starting material into an acid labile ether group such as tetrahydropyran-2-yloxy, tetrahydrofuran-2-yloxy, methoxy, ethoxy, or methoxymethylenoxy and especially t-butoxy. In general, however, the carbanion tends to react faster with the enol lactone groups.

Depending upon the particular enol lactone starting material, there is formed in some cases β,γ-carbocyclic ketone along with the α,β-unsaturated carbocyclic ketone. The β,γ-unsaturated ketone generally can be converted in high yield to the corresponding α,β-unsaturated carbocyclic ketone by isomerization using sodium hydroxide or other base in an organic solvent such as methanol.

The term "lower alkyl", as used herein, refers to a saturated aliphatic hydrocarbon group, branched or straight chain, containing one to six carbon atoms. The term "monoaryl" refers to phenyl and substituted phenyl such as tolyl, chlorophenyl, methoxyphenyl, and the like. Carboxylic acyl and carboxylic acyloxy refer to an acyl group and acyloxy group, respectively, containing less than 12 carbon atoms. Typical ester groups thus include acetate, propionate, butyrate, benzoate, mesitoate, cyclopentylpropionate, enanthate, trimethylacetate, t-butylacetate, adamantoate, and the like.

The novel process of the present invention is particularly useful for the production of carbocyclic ketones admirably suited for the synthesis of steriods. One application of the process of the present invention is illustrated below in a novel route for the synthesis of 19-nor steroids wherein R' is t-butyl and R⁴ is lower alkyl.

In the practice of the above process, the novel tricarbocyclic enol lactone (I') is reacted with the anion of 4-cycloethylenedioxypentylphosphonate of the following formula

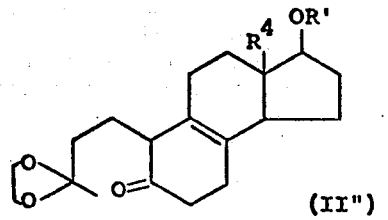

in which R is an defined above to yield a mixture of the α, β-unsaturated tricarbocyclic ketone (II') and the β,γ-unsaturated ketone (II'')

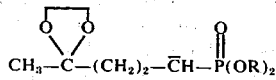
(II'')

in which R' and R⁴ are as defined above. This mixture is subjected to isomerization by treatment with dilute base, e.g. about 0.1 to 5% solution of an alkali hydroxide such as sodium or potassium hydroxide or an alkali alkoxide such as sodium methoxide, and the like, in a lower alcohol such as methanol or other organic sol-

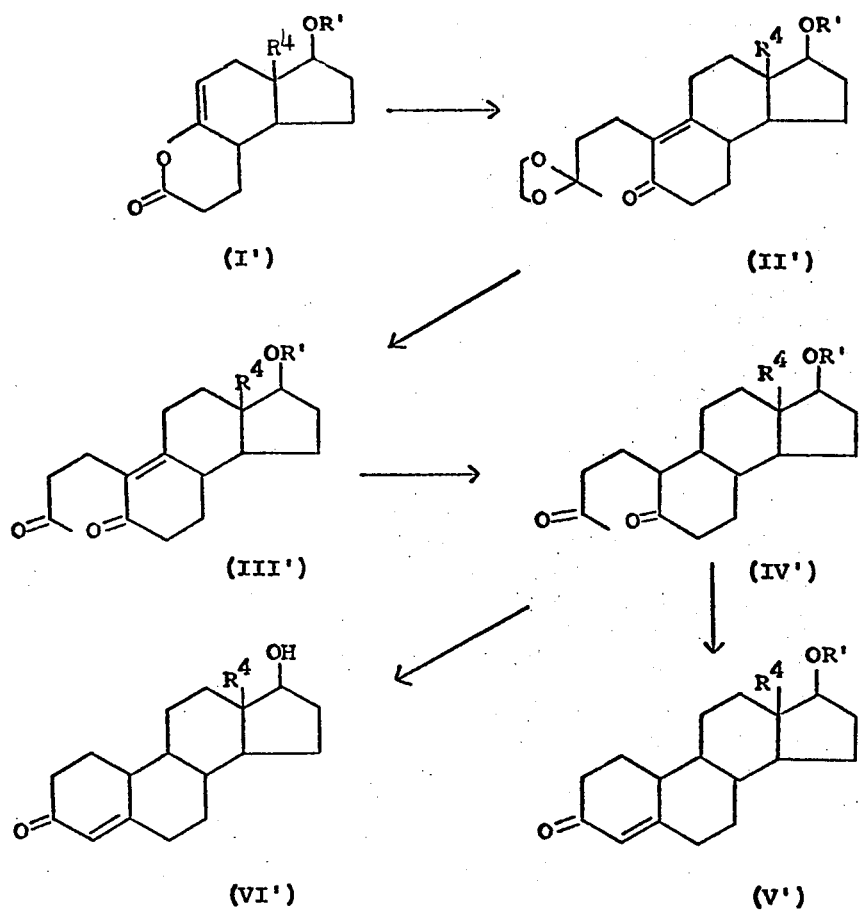

vent to yield only the α,β-unsaturated ketone (II') which is treated with aqueous organic acid such as acetic acid to yield the dione (III'). The dione (III') is subjected to catalytic hydrogenation using, e.g. palladium-on-carbon or barium sulfate to yield the saturated dione (IV'). The saturated dione is cyclized using either acid to afford 19-nortestosterone (VI') or using base to yield the t-butyl ether of 19-nortestosterone (V'). Cyclization with acid is accomplished with a mineral acid such as sulfuric acid or hydrochloric acid with concomitant removal of the t-butyl group. Suitable bases for cyclization include the alkali hydroxides such as sodium hydroxide. The 19-nor steroids of formulas V' and VI' are useful anabolic agents and intermediates for preparing other useful steroids such as 17α-ethynyl-17β-hydroxyestr-4-en-3-one (U.S. Pat. No. 2,744,122) by oxidation followed by ethynylation.

The following examples are provided to illustrate the present invention. Temperature in degrees Centigrade.

EXAMPLE 1

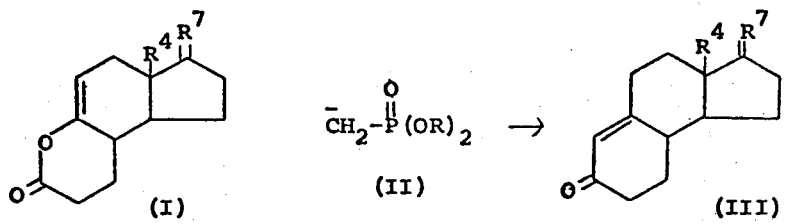

In the above formulas, R and $R^4$ are as defined above and $R^7$ is oxo or the lower alkylenedioxy or ketal thereof or the group

in which $R^8$ is hydroxy or the carboxylic ester or labile ether thereof.

To a solution of 1 g. of dimethyl methylphosphonate in 30 ml. of dry tetrahydrofuran under nitrogen and cooled to −78°, there is added one equivalent of n-butyl lithium in hexane with stirring. After about 10 minutes at −78°, one equivalent of the tricyclic enol lactone I ($R^4$ is methyl; $R^7$ is

in which $R^8$ is benzoyloxy) in 35 ml. of dry tetrahydrofuran is added. The reaction mixture is allowed to rise to room temperature and stand for about two hours. The reaction mixture is diluted with water and extracted with ether. The ether extracts are combined, washed with water, dried and evaporated under reduced pressure to give the tricarbocyclic ketone III ($R^4$ is methyl; $R^7$ is

in which $R^8$ is benzoyloxy) which can be further purified by chromatography, if desired.

The tricarbocyclic ketone (III) can be used to prepare therapeutically useful 19-nor or $\Delta^{1,3,5(10)}$-steroids using the procedure of, for example, U.S. Pat. No. 3,150,152.

The process of Example 1 is repeated with the exception of using dimethyl ethylphosphonate in place of dimethyl methylphosphonate and there is obtained the α,β-unsaturated tricarbocyclic ketones of formula IV which can be used to prepare Δ⁴-androstenes or retrosteroids using the method of Velluz et al., Tetrahedron, Suppl. 8, part II, pp. 495–505 (1966).

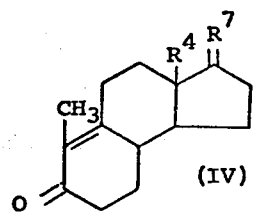

EXAMPLE 2

To a solution of 4 g. of diethyl 4-cycloethylenedioxypentylphosphonate V (R is ethyl) in 50 ml. of dry monoglyme under nitrogen and cooled to about −80°, there is added one equivalent of n-butyl lithium in hexane with stirring. After about five minutes at −80°, one equivalent of the trycyclic enol lactone I ($R^4$ is methyl; $R^7$ is

in which $R^8$ is benzoyloxy) in 75 ml. of dry monoglyme is added and the reaction mixture allowed to rise to room temperature. The reaction mixture is allowed to stand for about 2.5 hours and then diluted with water. The mixture is extracted with ether and the ether extracts combined, washed, dried and evaporated under reduced pressure to give the tricarbocyclic ketone VI ($R^4$ is methyl; $R^7$ is

in which $R^8$ is benzoyloxy) which can be further purified by chromatography on alumina.

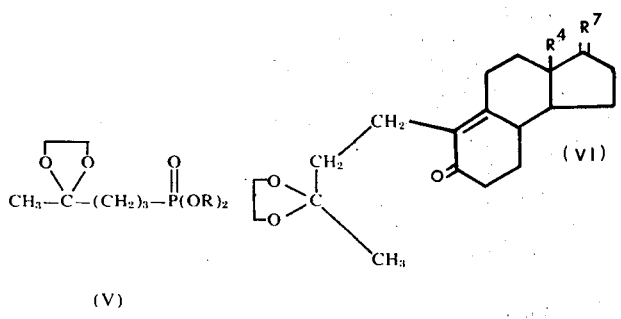

(V)

The mono-substituted methylphosphonate (V) can be prepared using the following procedure.

To a solution of 5.5 g. of pure sodium hydride in 200 ml. of dry tetrahydrofuran under nitrogen, there is added one equivalent of dry diethyl phosphite. The mixture is cooled in an ice-bath and stirred at 0° for 1.5 hours. One equivalent of the ethylene ketal of 1-bormopentan-4-one in 60 ml. of dry tetrahydrofuran is added and the mixture stirred for 15 minutes at 0° and allowed to stand 16 hours at room temperature. The mixture is then heated under reflux for three hours, cooled and filtered. The filtrate is concentrated under reduced pressure and the concentrate taken up in ether. This mixture is shaken with saturated aqueous sodium chloride and then separated. The organic layer is separated and concentrated under reduced pressure to give diethyl 4,4-ethylenedioxypentylphosphonate (V) (R is ethyl) which is purified by distillation in vacuo (b.p. 115° at 0.05 mm.).

By using other phosphites, e.g. dimethyl phosphite, dibenzyl phosphite or diphenyl phosphite, in place of diethyl phosphite in the above procedure, the corresponding di-substituted phosphonates are obtained.

EXAMPLE 3

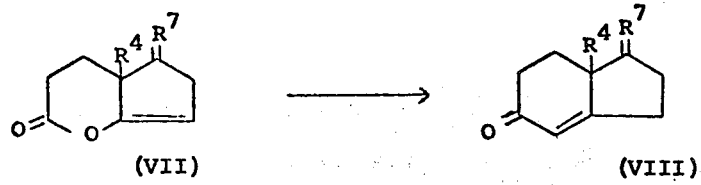

To a suspension of 2 g. of dimethyl methylphosphonate in 50 ml. of dry tetrahydrofuran at −78° under nitrogen, there is added one equivalent of n-butyl lithium in hexane with stirring. After about five minutes, there is added one equivalent of bicyclic enol lactone VII (R$^4$ is methyl; R$^7$ is

R$^8$
| ... H in which R$^8$ is benzoyloxy) in 50 ml. of dry tetrahydrofuran while maintaining the temperature at about −78°. The reaction mixture is allowed to warm to room temperature and to stand at room temperature for 3 hours. The reaction mixture is diluted with water and then extracted with ether. The ether extracts are combined, washed, dried and evaporated under reduced pressure to give the bicarbocyclic ketone VIII (R$^4$ is methyl; R$^7$ is

R$^8$
| ... H in which R$^8$ is benzoyloxy) which can be further purified by chromatography or fractional distillation.

The α,β-unsaturated bicarbocyclic ketones of formula VIII are useful intermediates for the synthesis of steroids using the method of, for example, Whitehurst et al., U.S. Pat. No. 3,317,566.

The bicyclic enol lactones of formula VII can be prepared using the following typical procedure or the method of French Pat. No. 1,496,817 (1966).

A mixture of 0.3 g. of 2-methylcyclopentane-1,3-dione, 0.33 ml. of methylacrylate and 0.1 g. of potassium t-butoxide in 200 ml. of t-butanol is allowed to stand at about 20°C for 72 hours. The reaction mixture is washed with water, dilute sodium hydroxide and then water to neutral, dried and evaporated to give 2-methyl-2-(β-carbomethoxyethyl)cyclopentane-1,3-dione which is purified by distillation.

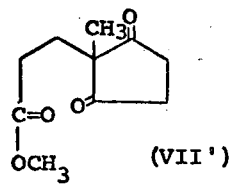

(VII')

The above prepared diketoester is then hydrolyzed to the acid by treatment with 1% potassium carbonate in warm methanol:water (1:1) for 8 hours. A total of 5 g. of this acid is mixed with 50 ml. of acetic anhydride containing 2 g. of anhydrous sodium acetate and the mixture boiled for 5 hours. The acetic anhydride is then removed by distillation in vacuo to furnish a residue which is poured into water and extracted with ethyl acetate. THe ethyl acetate extracts are combined, washed neutral with water, dried and evaporated. Purification of the resulting residue by vacuum distillation affords 1.2 g. of the enol lactone VII (R⁴ is methyl; R⁷ is oxo).

A mixture of 5 g. of the diketoester (VII'), 100 ml. of tetrahydrofuran and 1.3 molar equivalents of lithium tri-t-butoxyaluminum hydride is heated at reflux until the hydride reagent is consumed. The reaction mixture is cooled, diluted with concentrated aqueous sodium sulfite solution and the resulting clear supernatant decanted and evaporated. The resulting residue is purified by chromatography on alumina to furnish 1.3 g. of the following alcohol:

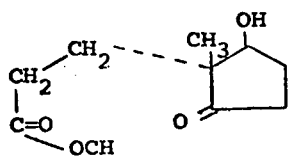

which is converted into the corresponding benzoate by treatment with benzoyl chloride in pyridine. The methyl ester is hydrolyzed to the acid which is then cyclized by the procedure described above to furnish the enol lactone of formula VII wherein R⁴ is methyl and R⁷ is

in which R⁸ is benzoyloxy.

By using 2-ethylcyclopentane-1,3-dione and 2-propylcyclopentane-1,3-dione in place of 2-methylcyclopentane-1,3-dione in the above procedure, the corresponding enol lactones wherein R⁴ is ethyl and propyl, respectively, are obtained. The 2-lower alkylcyclopentane-1,3-diones can be prepared according to the method of U.S. Pat. No. 3,318,922.

EXAMPLE 4

The process of Example 3 is repeated with the exception of using an equivalent amount of the phosphonate of formula IX (R is ethyl; R² is hydrogen; R³ is methyl) in place of dimethyl methylphosphonate and the substituted bicarbocyclic ketones (X) are obtained.

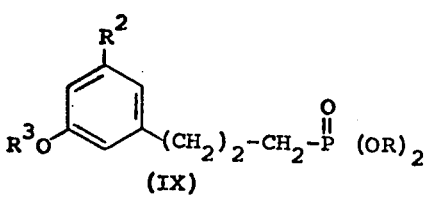

In the above formulas, R, R⁴ and R⁷ are as defined hereinabove, R² is hydrogen or a lower alkoxy of 1 to 6 carbon atoms and R³ is lower alkyl.

By using other phosphonates of formula IX in the above proess, the correspondingly substituted α,β-unsaturated bicarbocyclic ketones of formula X are obtained.

The phosphonates of formula IX can be obtained by using an equivalent amount of the bromide (XI) in place of the ethylene ketal of 1-bromopentan-4-one in the procedure set out in Example 2. The bromide (XI) can be prepared from the corresponding acid by the following procedure.

Ten grams of m-methoxycinnamic acid in 100 ml. of ethanol is hydrogenated with 0.5 g. of pre-reduced 10% palladium-on-charcoal until the uptake of hydrogen ceases. The catalyst is removed by filtration and the filtrate evaporated to yield 3-(m-methoxyphenyl)propionic acid.

A solution of 5 g. of the foregoing propionic acid in 100 ml. of tetrahydrofuran is added cautiously to a boiling solution of 250 ml. of tetrahydofuran containing 3 g. of lithium aluminum hydride. The reaction mixture is refluxed overnight with stirring and then cooled and the excess of hydride decomposed by the cautious addition of ethyl acetate and then saturated sodium sulfate. The resulting clear solution is decanted and dried over sodium sulfate. The solvent remaining is removed by distillation to give 3-(m-methoxyphenyl)-propanol which is purified by distillation in vacuo. One gram of this propyl alcohol in 50 ml. of benzene is boiled with a slight excess of phosphorus pentabromide until thin layer chromatography no longer indicates the presence of starting alcohol. The reaction mixture is cooled, washed with water and dilute sodium carbonate solution, dried over sodium sulfate and concentrated to dryness to give 3-(m-methoxyphenyl)propyl bromide (XI) (R² is hydrogen; R³ is methyl) which is purified by distillation.

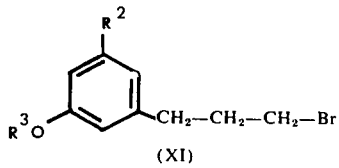

By using 3,5-dimethoxycinnamic acid in place of m-methoxycinnamic acid, the bromide (XI) in which R² is methoxy and R³ is methyl is obtained.

The bicarbocyclic ketones of formula X above can be converted into estra-1,3,5(10),8,14-pentaenes by treatment with p-toluenesulfonic acid in benzene or by the method of U.S. Pat. No. 3,317,566.

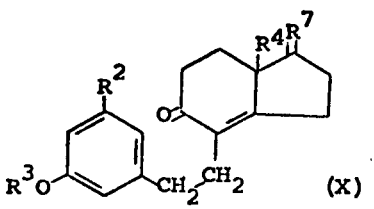

EXAMPLE 5

To a suspension of 4 g. of dibutyl methylphosphonate in 75 ml. of dry monoglyme at about −78° under nitrogen, there is added with stirring one equivalent of n-butyl lithium in hexane. After about 10 minutes, there is added one equivalent of 17β-acetoxy-4-oxa-androst- 5-en-3-one in 75 ml. of dry tetrahydrofuran while maintaining the temperature at about −78°. The reaction mixture is allowed to warm to room temperature and then left to stand for about four hours. The reaction mixture is diluted with water and extracted with ether. The ether extracts are combined, washed, dried and evaporated to give testosterone acetate (17β-acetoxyandrost-4-en-3-one) which can be purified by chromatography.

By using diethyl ethylphosphonate in the process of this example, the correspondingly substituted tetracarbocyclic compound is obtained, i.e. 4-methyl testosterone acetate.

By using other steroidal enol lactones in the above process in place of 17β-acetoxy-4-oxa-androst-5-en-3-one as the starting material, e.g. 4-oxa-cholest-5-en-3-one, 3-ethoxy-17-oxa-D-homoestra-1,3,5(10),15-tetraen-17-one, 17,20;20,21-bis-methylenedioxy-11β-hydroxypregn-5-en-3-one, and the like, the corresponding α,β-unsaturated tetracarbocylic ketone is obtained, e.g. cholest-4-en-3-one, 3-ethoxy-D-homoestra-1,3,5(10), 14-pentaen-17-one, and 17,20;20,21-bismethylenedioxy-11β-hydroxypregn-4-en-3-one.

EXAMPLE 6

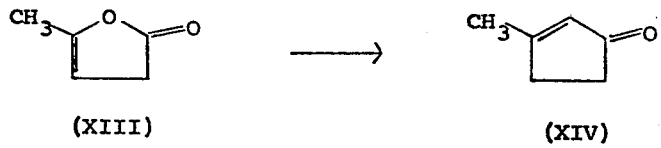

(XIII)          (XIV)

To a suspension of 2 g. of dibenzoyl methylphosphonate in 30 ml. of dry tetrahydrofuran cooled to a temperature of about −60° under nitrogen, there is added 1.1 equivalents of phenyl lithium in hexane with stirring. After about 5 minutes, there is added, while maintaining the temperature at about −60°, 0.95 equivalents of angelica lactone (XIII) in 40 ml. of dry tetrahydrofuran. The reaction mixture is allowed to warm to room temperature and then left to stand for about 2 hours. The mixture is then diluted with water and the product extracted with ether to give 3-methylcyclopent-2-en-1-one (XIV) which can be purified by vacuum distillation.

By using a mono-substituted methylphosphonate, for example, diethyl ethylphosphonate in the above process, the corresponding 2-substituted α,β-unsaturated cyclopentone is obtained, e.g. 2,3-dimethylcyclopent-2-en-1-one.

EXAMPLE 7

To a solution of 5 g. of dimethyl methylphosphonate in 100 ml. of dry tetrahydrofuran cooled to about −78° under nitrogen, there is added with stirring one equivalent of n-butyl lithium in hexane. After about 10 minutes, there is added one molar equivalent of 3-methoxy-16-oxaestra-1,3,5(10),8,14-pentaen-17-one in dry tetrahydrofuran while maintaining the temperature at about −78°. The mixture is allowed to warm to room temperature and then left to stand at room temperature for 5 hours. The mixture is diluted with water and then extracted with ether. The ether extracts are combined and concentrated to furnish a residue which is chromatographed on neutral alumina eluting with benzene to afford 3-methoxy-14β-estra-1,3,5(10),8,15-pentaen-17-one and 3-methoxy-14α-estra-1,3,5(10),8,15-pentaen-17-one which can be further purified by recrystallization from aqueous methanol.

0.5 g. of 3-methoxy-14α-estra-1,3,5(10),8,15-pentaen-17-one in 25 ml. of ethanol is reduced catalytically with 50 mg. of 5% palladium-on-charcoal until a molar equivalent of hydrogen is taken up. The catalyst is filtered off and the filtrate evaporated to dryness to yield the known 3-methoxyestra-1,3,5(10),8-tetraen-17-one which can be converted into estrone methyl ether by procedures outlined in Chemistry & Industry (London), 1022 (1960) or into 19-nor-Δ⁴-steroids using the procedure of, for example, U.S. Pat. No. 3,318,922.

By repeating the above process using other 16-oxa steroids of the formula XV, e.g. 3-methoxy-15-methyl-16-oxaestra-1,3,5(10),6,8,14-hexaen-17-one as the tetracyclic enol lactone starting material, the corresponding steroidal ketone (tetracarbocyclic ketone) of the formula XVI is obtained, e.g. 3-methoxy-15-methyl-14α-estra-1,3,5(10),6,8,15-hexaen-17-one and 3-methoxy-15-methyl-14β-estra-1,3,5(101,6,8,15-hexaen-17-one.

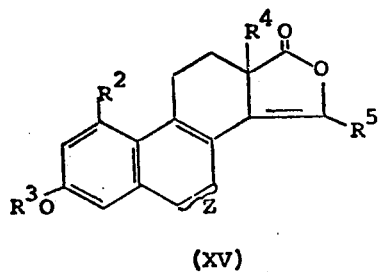      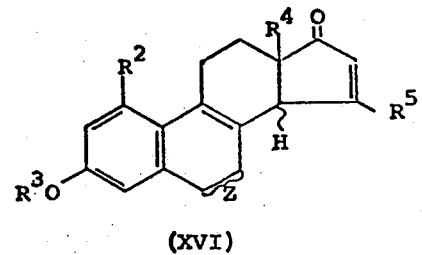

(XV)          (XVI)

In the above formulas, $R^2$, $R^3$ and $R^4$ are as defined hereinabove, $R^5$ is hydrogen or methyl and Z is a carbon to carbon single or double bond between C-6 and C-7.

The tetracarbocyclic ketones (XVI) can be converted into therapeutically useful steroids using the procedures described and referenced above. The 15-methyl substituted steroids can be used in the same manner as the corresponding 15-unsubstituted steroids.

The tetracyclic enol lactones of formula XV can be prepared according to the method of Simpson et al., Tetrahedron Letters, 3209 (1967) or U.S. Pat. No. 3,309,383.

EXAMPLE 8

The process of Example 2 is repeated with the exception that the phosphonate employed is a phosphonate of formula XVII and there are obtained the substituted tricarbocyclic ketones XVIII which are useful in the synthesis of valuable 2-methyl-19-nor steroids and 2-methylandrostene steroids using the procedure of, for example, Velluz et al., ibid.

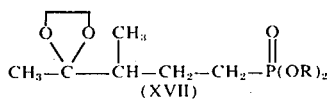
(XVII)

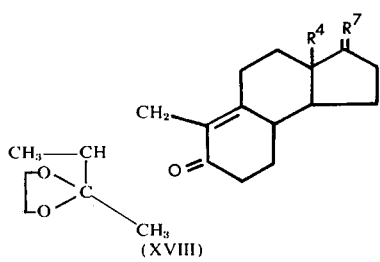
(XVIII)

The mono-substituted methylphosphonates of formula XVII can be prepared by the procedure described in Example 2 using the ethylene ketal of 1-bromo-3-methylpentan-4-one as the starting material. This bromide starting material can be prepared according to the following procedure.

A mixture of 0.5 moles of 1-acetoxypentan-4-one and 0.5 moles of piperidine in benzene is refluxed using a water separator until no more water distills from the reaction mixture. The reaction mixture is then cooled, washed and dried to afford the 4-piperidyl-1-acetoxypent-3-ene (XIX). A mixture of 5 g. of XIX in 100 ml. of dioxane is treated with an excess of methyl iodide at 20°C for 18 hours and then heated at 70°C for 6 hours. The reaction mixture is concentrated to a small volume, diluted with water and 1-acetoxy-3-methylpentan-4-one isolated by extraction with ethyl acetate. A mixture of 0.5 g. of this ketone, 100 mg. of p-toluenesulfonic acid, 3 ml. of ethyleneglycol and 100 ml. of benzene is refluxed using a water separator for 24 hours. The reaction mixture is cooled and then 100 ml. of ethanol and 2 g. of potassium hydroxide are added. This mixture is refluxed for 6 hours, cooled, diluted with water and the corresponding ethylene ketal is isolated by extraction with ethyl acetate. A solution of 0.1 moles of the ketal in 50 ml. of dimethylformamide containing 0.1 moles of triphenylphosphine is reacted with 0.1 moles of carbon tetrabromide at room temperature for 18 hours. The mixture is diluted with water and extracted with ether. The ether extracts are combined, washed with water, dried and evaporated. The residue is chromatographed on 400 g. of alumina eluting with hexane-benzene and benzene to give the ethylene ketal of 1-bromo-3-methylpentan-4-one.

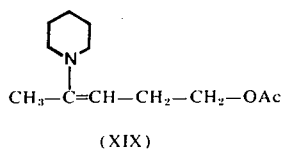
(XIX)

EXAMPLE 9

A mixture of 10 g. of 1-chloropentan-4-one, 100 ml of ether and 1 g. of lithium aluminum hydride is allowed to stand at 20°C for 20 hours. The reaction mixture is diluted with water and separated. The organic phase is washed with water, dried and evaporated to give 1-chloropentan-4-ol which is purified by distillation. Two ml. of dihydropyran is added to a solution of 1 g. of 1-chloropentan-4-ol in 15 ml. of benzene. About 1 ml. is removed by distillation to remove moisture and 0.4 g. of p-toluenesulfonic acid is added to the cooled solution. This mixture is allowed to stand at room temperature for four days and is then washed with aqueous sodium carbonate solution and water, dried and evaporated to yield 4-(tetrahydropyran-2'-yloxy)-1-chloropentane which is subjected to the procedure described in Example 2 to give the phosphonate (XX).

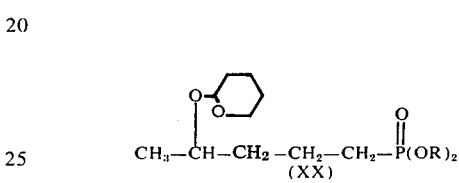
(XX)

The process of Example 2 is repeated with the exception that the phosphonate of formula XX (R is ethyl) is used in place of the phosphonate V and there is obtained the tricarbocyclic ketones (XXI) which can be converted into 19-nor steroids.

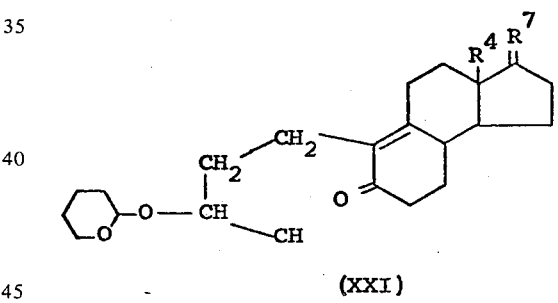
(XXI)

EXAMPLE 10

To a suspension of 4 g. of diethyl (4-chloropentyl-3-enyl)phosphonate in 50 ml. of dry monoglyme at about −78°, there is added 1.1 equivalents of butyl lithium in hexane with stirring under nitrogen. After about 10 minutes, there is added 1.1 equivalents of the tricyclic enol lactone I ($R^4$ is methyl; $R^7$ is

...H in which $R^8$ is benzoyloxy) in 60 ml. of dry monoglyme while maintaining the temperature at about −78°. The reaction mixture is allowed to warm to room temperature and then left to stand at room temperature for about 2 hours. The reaction mixture is diluted with water and then extracted with ether. The ether extracts are combined, washed, dried over magnesium sulfate and evaporated under reduced pressure to afford the α,β-unsaturated tricarbocyclic ketone XXII ($R^4$ is methyl; Ac is benzoyl) which can be purified further by chromatography on alumina.

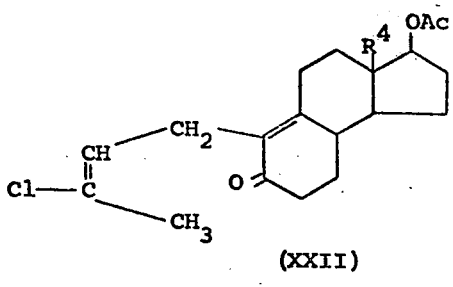

(XXII)

The tricarbocyclic ketone (XXII) is a useful intermediate for the synthesis of 19-nor steroids using the procedure of U.S. Pat. Nos. 3,050,550, 3,019,252 or 3,150,152.

The phosphonate used in the process of this example can be prepared according to the following procedure.

A mixture of 10 g. of 1-bromopentan-4-one, 100 ml. of carbon tetrachloride and 5 g. of phosphorus pentachloride is refluxed for 10 hours. The reaction mixture is then cooled, washed with dilute sodium carbonate and water, dried over magnesium sulfate and evaporated to give 1-bromo-4-chloropent-3-ene which is purified by distillation and converted into the phosphonate by the procedure described in Example 2.

EXAMPLE 11

To a suspension of 4 g. of diethyl 4,4-dimethoxybutylphosphonate in 50 ml. of dry monoglyme at about −70° under nitrogen, there is added one equivalent of phenyl lithium in hexane with stirring. After about 5 minutes, there is added 1.0 equivalent of the bicyclic enol lactone VII ($R^4$ is ethyl; $R^7$ is

...H in which $R^8$ is benzoyloxy) in 50 ml. of dry monoglyme while maintaining the temperature at about −70°. The reaction mixture is allowed to warm to room temperature and then allowed to stand at room temperature for 3.5 hours. The reaction mixture is then diluted with water and extracted with ether. The ether extracts are combined, washed, dried over magnesium sulfate and evaporated under reduced pressure. The residue is chromatographed on silica gel to afford the α,β-unsaturated bicarbocyclic ketone XXIII ($R^4$ is ethyl; Ac is benzoyl).

A mixture of 1 g. of the above bicarbocyclic ketone, 25 ml. of dioxane and 1 ml. of 5% aqueous HCl is boiled 15 minutes. The reaction mixture is allowed to cool, poured into water and the resulting mixture separated. The organic phase is evaporated to dryness to furnish the corresponding aldehyde which is taken up in 20 ml. of acetone, cooled to 0°C and a slight molar excess of Jones reagent (prepared by mixing 26 g. of chromium trioxide with 23 ml. of concentrated sulfuric acid and diluting with water to 100 ml.). Upon completion of the oxidation as followed by thin layer chromatography, the reaction mixture is diluted with water and then extracted with ethyl acetate. The ethyl acetate extracts are combined, washed with water, dried and evaporated under reduced pressure to afford the acid (XXIV) ($R^4$ is ethyl; Ac is benzoyl) which is a valuable intermediate for the synthesis of known 19-nor-$\Delta^4$ and $\Delta^{5(10)}$-steroids useful as therapeutic agents using the procedure of, for example, Belgian Pat. No. 629,251 (1963); French Pat. No. 1,465,400 (1965) or Velluz et al., ibid.

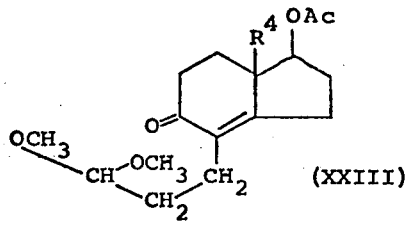 (XXIII)

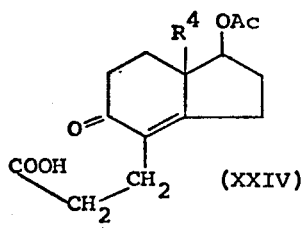 (XXIV)

The diethyl 4,4-dimethoxybutylphosphonate employed in this example can be obtained according to the following procedure.

To 0.5 moles of diethylmalonate in 0.5 liters of dry benzene is added 0.5 moles of sodium hydride cautiously and the mixture stirred until hydrogen evolution ceases. Then 0.5 moles of bromoacetaldehydedimethylacetal [$(CH_3O)_2$—CH—$CH_2$—Br] in 100 ml. of benzene is added and the mixture stirred overnight followed by refluxing for 2 hours. The reaction mixture is cooled, washed with water and purified by vacuum distillation to give β,β-dimethoxyethylmalonic acid diethyl ester. A mixture of 5 g. of this ester in 100 ml. of ethanol containing 5 g. of sodium hydroxide is heated under reflux until evolution of carbon dioxide ceases. The reaction mixture is then saturated with carbon dioxide and evaporated to dryness under vacuum. The residue is suspended in 50 ml. of dry dimethylformamide to which is added a large excess of methyl iodide. The reaction mixture is stirred at room temperature for about 24 hours and then poured into water. The resulting mixture is extracted with ether and the ether extracts combined, washed with water and evaporated to give 4,4-dimethoxybutyric acid methyl ester which is purified by distillation. A mixture of 4 g. of this methyl ester, 50 ml. of dry tetrahydrofuran and 1.1 equivalents of lithium aluminum hydride is refluxed overnight. The reaction mixture is allowed to cool and then filtered with water. This mixture is extracted with ether and the ether extracts are combined, washed, dried and evaporated to dryness to afford 4,4-dimethoxybutanol [$(CH_3O)_2$—CH—$CH_2$—$CH_2$—$CH_2$—OH].

A solution of 0.1 moles of 4,4-dimethoxybutanol in 50 ml. of dimethylformamide containing 0.1 moles of triphenylphosphine is allowed to react for 18 hours with 0.1 moles of carbon tetrabromide. The mixture is diluted with water and extracted with ether. The ether extracts are combined, washed with water, dried and evaporated to a crude product which is purified by distillation to yield 4,4-dimethoxybutylbromide. This bromide is then converted into the diethyl phosphonate using the procedure described in Example 2.

EXAMPLE 12

The process of Example 11 is repeated using a phosphonate (XXV) as the phosphonate reagent and n-butyl lithium as the base and the corresponding carbocyclic ketone (XXVI) is obtained which can be converted into valuable 6-methyl steroids.

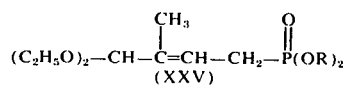
(XXV)

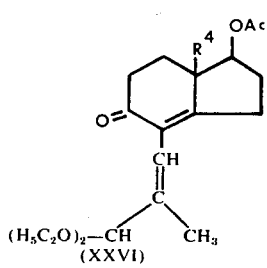
(XXVI)

Conversion of the carbocyclic ketone (XXVI) into 6-methyl steroids can be accomplished by, for example, catalytic reduction using 5% palladium-on-charcoal in ethanol to the intermediate (XXVII) which is converted into the free acid (XXVIII) using the procedure described in Example 11. The free acid can then be cyclized to the tricyclic enol lactone (XXIX) using the method of Velluz et al., ibid. The enol lactone (XXIX) can then be treated as described in Example 1 and 2 to obtain the corresponding tricarbocyclic ketone which can be converted into 6-methyl steroids using the procedures referenced therein.

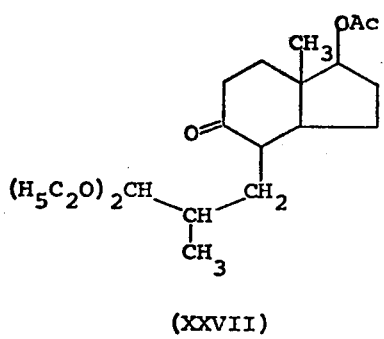
(XXVII)

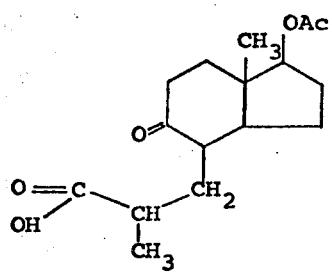
(XXVIII)

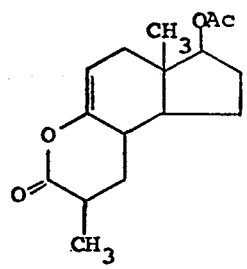
(XXIX)

EXAMPLE 13

Diethyl methylphosphonate (1.94 g.) suspended in 50 ml. of dry tetrahydrofuran is treated with 1.1 equivalents of butyl lithium in hexane under nitrogen at about −78°. After 10 minutes, one equivalent of benzalphthalide in 10 ml. of tetrahydrofuran is added while maintaining the temperature at about −78°. The reaction mixture is allowed to warm to room temperature and then left to stand at room temperature for 3 hours. The reaction mixture is diluted with water and then extracted with ether. The ether extracts are combined, washed with water, dried and the solvent removed under vacuum. The residue is chromatographed on silica eluting with methylene chloride:hexane (4:1) to afford 3-benzylind-2-en-1-one and a small amount of starting material.

EXAMPLE 14

The process of Example 3 is repeated with the exception that the phosphonate (XXX) (R is ethyl) is used in place of dimethyl methylphosphonate and there is obtained the substituted bicarbocyclic ketone (XXXI) ($R^4$ is methyl; Ac is benzoyl).

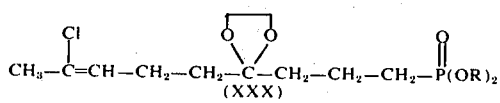
(XXX)

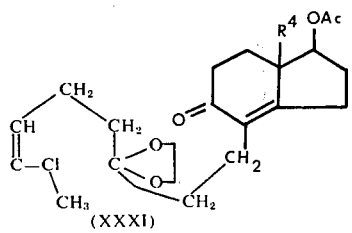

The novel bicarbocyclic ketone (XXXI) is useful for the preparation of the known tricarbocyclic ketones (XXII) which can be used to prepare 19-nor steroids. Thus, hydrogenation of the bicarbocyclic ketone using, for example, 5% palladium-on-charcoal in ethanol followed by deketalization under mild condition such as 1% sulfuric acid in dioxane with refluxing for one hour furnishes the intermediate (XXXII) which can be cyclized using, e.g. a base as described by, e.g. Velluz et al., ibid., U.S. Pat. Nos. 3,102,145 and 3,150,152, or French Pat. No. 1,480,247, to furnish the tricarbocyclic ketone XXII (Ac is hydrogen).

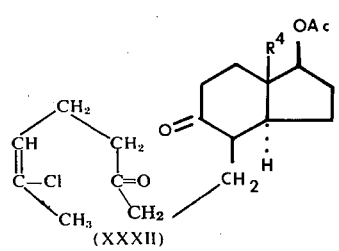

The phosphonate (XXX) can be prepared using the following procedure.

A mixture of 0.5 moles of 1,3-dithiane and 300 ml. of tetrahydrofuran cooled to −30° is treated with 0.5 molar equivalents of 1.5 molar n-butyl lithium in hexane under nitrogen and stirred for 15 hours at −20°. Then 0.5 moles of the tetrahydropyranyl ether of 3-bromopropanol in 200 ml. of tetrahydrofuran is added slowly with stirring at −5° and then left for 14 hours at 0° under nitrogen. The resulting mixture is cooled to −30° and treated with an additional 0.5 molar equivalents of 1.5 molar n-butyl lithium in hexane. After 1.5 hours, 0.5 moles of 4-chloro-1-bromopent-3-ene in 200 ml. of tetrahydrofuran is added. The reaction mixture is left standing for 18 hours at 0° and then allowed to warm to room temperature for four hours. Water is added and the resulting mixture extracted with ether. The ether extracts are combined, washed with water, dried and concentrated. The resulting dialkylated thiane (XXXIII) is dissolved in methanol and stirred for two hours with 20 ml. of 1% oxalic acid solution. The reaction mixture is poured into water containing an excess of sodium carbonate solution and then extracted with ether to afford the corresponding free hydroxy compound. The free hydroxy compound is dissolved in dry ethylene glycol containing 0.5 g. of mercuric chloride. This reaction mixture is allowed to stand overnight and then heated to 60° for 5 hours. After cooling, water is added and the ketal (XXXIV) isolated by extraction with ether. A mixture of 2 g. of the ketal and 30 ml. of methylene chloride: pyridine (2:1) is cooled to −70° and then treated with one equivalent of tosylchloride in methylene chloride. The mixture is left standing at 0° for 18 hours and then allowed to warm to room temperature. The mixture is then diluted with water and the resulting tosylate isolated by extraction with methylene chloride and purified by chromatography on deactivated alumina. This tosylate (0.5 g.) in 25 ml. of acetone is refluxed for 24 hours with 0.5 g. of sodium iodide. After cooling, the reaction mixture is diluted with water and extracted with ether. The resulting crude iodide is treated with sodium hydride and diethyl phosphite as described in Example 2 to furnish the phosphonate (XXX) (R is ethyl).

Alternatively, the tosylate can be reacted with sodium hydride and diethyl phosphite using the procedure of Example 2 to obtain the phosphonate.

By repeating the preparation using other phosphites, e.g. dibutyl phosphite, dicyclohexyl phosphite, dimethyl phosphite or diphenyl phosphite in place of diethyl phosphite, the corresponding phosphonates are obtained.

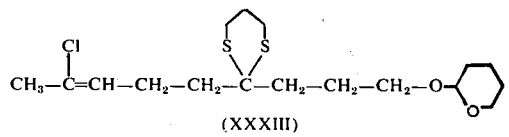

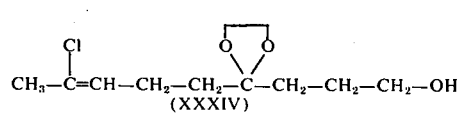

EXAMPLE 15

The process of Example 2 is repeated using as the phosphonate reagent, the phosphonate of formula XXXV (R is ethyl) and there is obtained the tricarbocyclic ketone (XXXVI) (Ac is benzoyl) which can be converted into 19-nor steroids or androstane steroids by methods disclosed in the Journal of American Chemical Society, 82, No. 21, 5464 (1967).

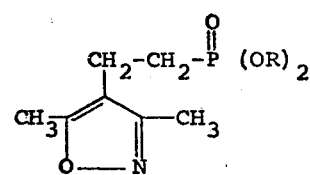

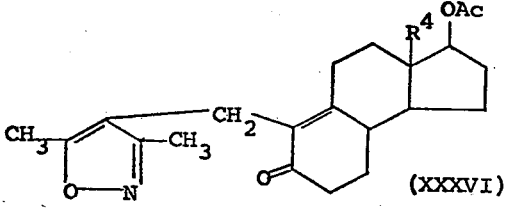

The phosphonate (XXXV) can be obtained according to the following outlined procedure.

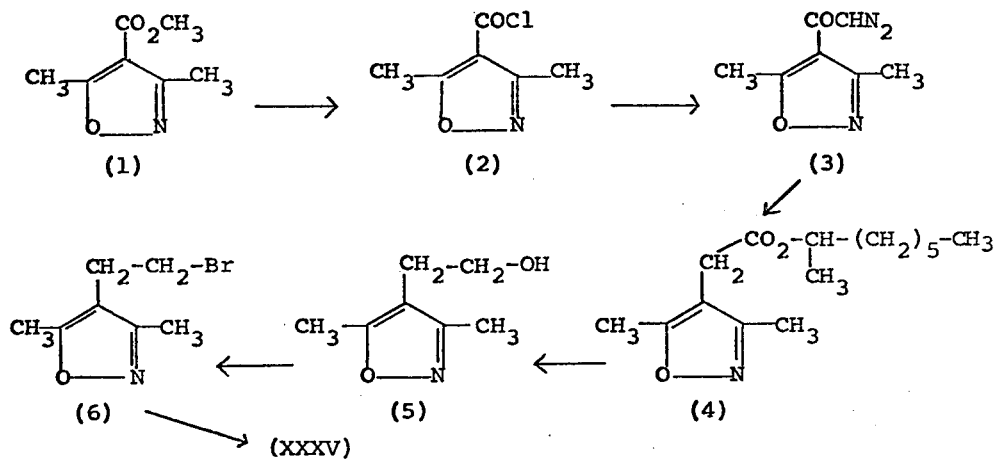

Ten grams of the isoxazole 1) lis heated at reflux with 200 ml. of 1% sodium hydroxide in methanol for five hours. The reaction mixture is then acidified to pH 3 with HCl and the acidified mixture is then concentrated to a small volume under reduced pressure. Water is added and the acid isolated by extraction with ethyl acetate. The crude acid (9 g.) is taken up in methanol and treated with one equivalent of sodium methoxide. The alcohol is evaporated and the residue dried under reduced pressure. The residue is then suspended in dry benzene and treated at 0°C with an excess of oxalyl chloride. After the evolution of gas ceases, the reaction mixture is allowed to warm to room temperature and the excess of oxalyl chloride removed by evaporation of the solvent medium to dryness. The resulting acid chloride (2) is taken up in benzene and treated with an excess of ethereal diazomethane. After the formation of the diazoketone is complete, the ether is removed and the resulting diazoketone heated under reflux in octane-2-ol until nitrogen evolution ceases. The crude product is purified by distillation and reduced with an excess of lithium aluminum hydride in 200 ml. of tetrahydrofuran under reflux. The reaction mixture is decomposed by cautious addition of ethyl acetate and the inorganic salts precipitated by the addition of concentrated sodium sulfate solution. The solution is then filtered and evaporated to yield the alcohol (5) which is purified by distillation. The alcohol (5) is then treated with phosphorus tribromide in benzene to give the bromide (6) which is converted into the phosphonate (XXXV) by the procedure described in Example 2.

Example 16

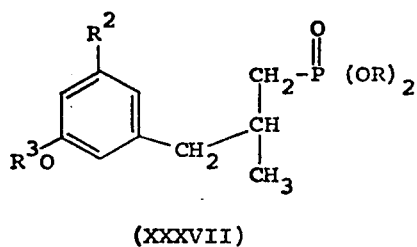

(XXXVII)

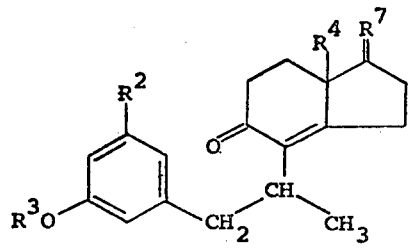

(XXXVIII)

The process of Example 3 is repeated with the exception that dimethyl methylphosphonate is replaced with an equivalent amount of the phosphonate (XXXVII) (R is ethyl; $R^2$ is hydrogen; $R^3$ is methyl) and the corresponding substituted α,β-unsaturated bicarbocyclic ketones XXXVIII are obtained.

The bicarbocyclic ketones of formula XXXVIII are excellent intermediates for the production of valuable 7-methyl steroids using the procedures described in Example 4.

The phosphonates of formula XXXVII can be prepared according to the following outlined procedure wherein $R^2$, $R^3$ and X are as defined hereinabove.

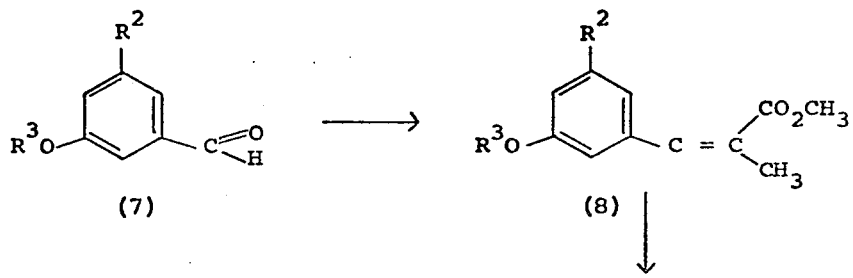

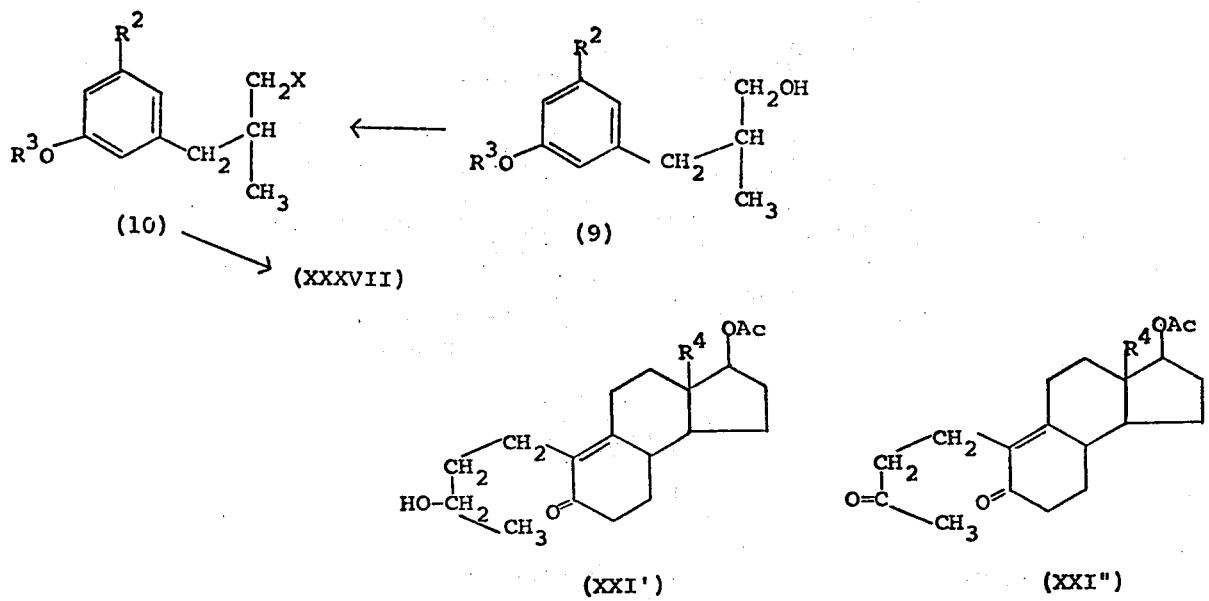

A solution of 0.6 moles of the aldehyde (7) and 0.5 moles of methyl α-bromopropionate in 80 ml. of dry benzene is added dropwise to 0.6 moles of zinc dust. After 15 ml. of the solution is added, the mixture is heated to initiate the reaction. The remaining portion of the solution is then added during 1 hour. The resulting mixture is cooled, washed with water, dried and then refluxed with 0.2 g. of p-toluenesulfonic acid for five hours. After cooling, the reaction mixture is washed with dilute sodium bicarbonate solution and water and then dried and purified by distillation to give 8. One gram of 8 in 25 ml. of ethanol is hydrogenated with 0.1 g. of 5% palladium/carbon catalyst until 1 molar equivalent of gas is taken up. The catalyst is filtered off and solvent evaporated to give 2-methyl-3-(substituted phenyl)propionic acid methyl ester. One gram of this ester in 100 ml. of tetrahydrofuran is reduced with 2 g. of lithium aluminum hydride until thin layer chromatography indicates the absence of starting ester. The reaction mixture is cooled, treated cautiously with an excess of ethyl acetate followed by saturated sodium sulfate solution. The organic layer is decanted off, dried with sodium sulfate and evaporated to give the alcohol (9) which is converted into the corresponding halide or tosylate (10) by procedures described herein (see Examples 4, 8 and 14). The halide or tosylate (10) is then converted into the phosphonate (XXXVII) using the procedure described in Example 2.

EXAMPLE 17

By subjecting the tricarbocyclic ketone (XXI) to acid hydrolysis conventionally used to remove a tetrahydropyranyl protecting group, e.g. dilute hydrochloric acid at room temperature, the corresponding free alcohol (XXI') is obtained which can be subjected to oxidation using, for example, chromium trioxide in pyridine at room temperature to give the corresponding carbonyl (XXI''). The tricarbocyclic (XXI'') can be converted into valuable estrogens using known procedures, see U.S. Pat. No. 3,150,152.

In the above formulas, R$^4$ and Ac are as defined hereinabove.

EXAMPLE 18

The process of Example 3 for the preparation of the bicyclic enol lactone (VII) is repeated with the exception that trifluoroacetyl chloride, acetyl chloride, and trimethylacetyl chloride is used in place of benzoyl chloride and there is obtained the corresponding carboxylic esters of VII, that is, the trifluoroacetate, acetate and trimethylacetate.

EXAMPLE 19

To 0.25 ml. of diethyl 4-cycloethylenedioxypentylphosphonate in 8 ml. of tetrahydrofuran at −78° under argon is added 1.6 molar equivalents of butyl lithium in 0.40 ml. of hexane with stirring. After 15 minutes at −78°, 0.14 g. of the enol lactone I' (R$^4$ is methyl) in 8 ml. of cold tetrahydrofuran is added. The solution is stirred for 0.5 hours at −78° and then set aside at room temperature for 6 hours. The solvent is removed under vacuum and the residue remaining is treated with saturated aqueous sodium chloride and extracted with ether to give a mixture of II' and II'' (R$^4$ is methyl). To the mixture of II' and II'' is added 2 g. of potassium hydroxide, 2 ml. of water and 25 ml. of methanol and the mixture refluxed 1.5 hours under nitrogen. Concentration under vacuum, dilution with saturated aqueous sodium chloride and isolation with ether yields solely II' (R$^4$ is methyl).

To 0.18 g. of II' is added 4 ml. of acetic acid and 0.5 ml. of water and the solution heated to 80° for 1.5 hours. The solution is concentrated under vacuum and isolation with ether yields III' (R is methyl) with the t-butyl group (R') intact. The α,β-unsaturated diketone III' in 10 ml. of 0.2% triethylamine in 95% aqueous ethanol is hydrogenated at room temperature and pressure over 5% palladium-on-charcoal until 1 equivalent of hydrogen is absorbed (about 15 minutes). The mixture is filtered and the filtrate evaporated to yield the saturated dione (IV').

A mixture of 20 mg. of the dione (IV'), 10 ml. of methanol, 1 ml. of water and 0.5 g. of potassium hydroxide is heated under reflux for 2.5 hours under nitrogen. The mixture is allowed to cool and then evaporated under vacuum. The residue is taken up in ether, washed, dried over sodium sulfate, and evaporated to dryness to yield the t-butyl ether of 19-nortestosterone (V'; $R^4$ is methyl).

A mixture of 15 mg. of the dione (IV'), 5 ml. of methanol, 1 ml. of water and 2 ml. of 37% hydrochloric acid is refluxed under nitrogen for 3 hours. The solvent is removed under vacuum and isolation with ether gave 19-nortestosterone (VI'; $R^4$ is methyl).

The following procedure is used for preparing the enol lactones of formula I' wherein R' and $R^4$ are as defined therein.

A mixture of 0.8 g. of the ester (XXXI'; $R^4$ is methyl), 50 ml. of ethanol, 10 ml. of water and 5 g. of potassium hydroxide is heated under reflux for 2.5 hours. Solvent is removed, water added, and extraction with ether. The aqueous phase is adjusted to pH 2 and the acid (XXXII') isolated with ether.

A mixture of 0.24 g. of the acid (XXXII'; $R^4$ is methyl), 0.6 g. of sodium acetate and 10 ml. of acetic anhydride is refluxed under nitrogen for 4 hours. The reaction mixture is evaporated under vacuum and the residue treated with ether and aqueous sodium bicarbonate. Isolation with ether gave the tricyclic enol lactone (I'; $R^4$ is methyl).

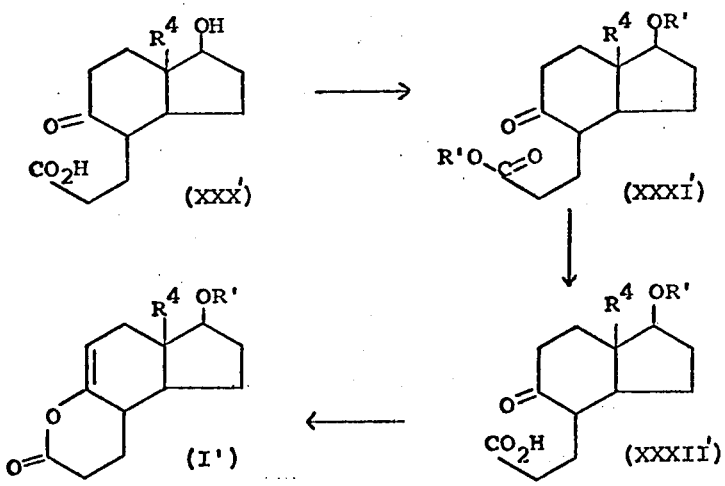

A suspension of 0.5 g. of the hydroxy acid (XXX'; $R^4$ is methyl) in 40 ml. of methylene dichloride is cooled to −70° and then 40 ml. of isobutylene and 0.6 ml. of 93% sulfuric acid are added. This reaction mixture is shaken for 17 hours in a pressure vessel. The vessel is then recooled to −70°, opened and the solution poured into aqueous sodium bicarbonate with stirring. Isolation with methylene dichloride gave the ester (XXXI').

The hydroxy acids (XXX') can be prepared using the procedure of Velluz et al., ibid. or French Pat. No. 1,465,400 (1965) by the reaction of the lower alkyl ester of 5-keto-6-heptenoic acid with a 2-loweralkylcyclopentane-1,3-dione (prepared by the method of U.S. Pat. No. 3,318,922) in the presence of base, e.g. triethylamine followed by cyclization with acid hydrolysis, reduction and hydrogenation.

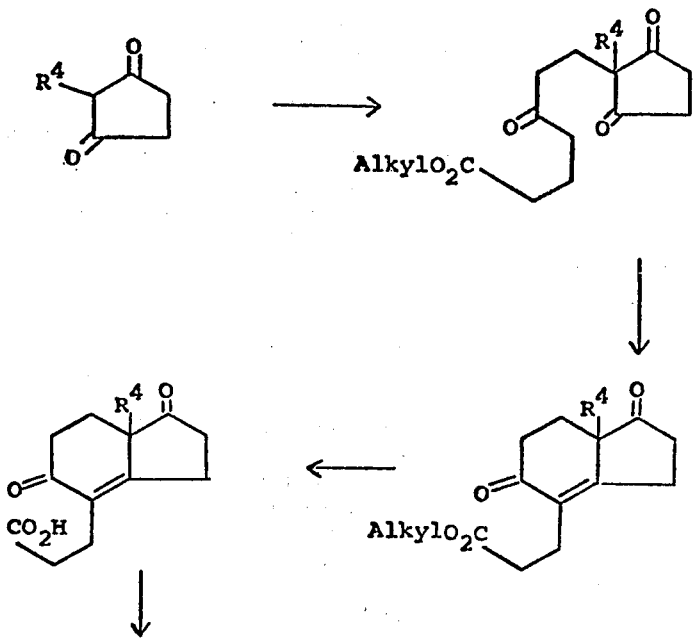

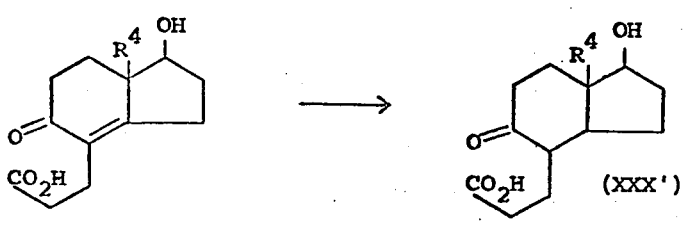

As an alternate method, the hydroxy acid can be prepared by reacting a bicyclic enol lactone of formula VII with diethyl 4, 4-dimethoxybutylphosphonate anion followed by hydrolysis, oxidation of the aldehyde to the acid and then hydrogenation with palladium-on-charcoal. The bicyclic enol lactones (VII) can be obtained according to the method of French Pat. No. 1,496,817 (1966) using a 2-lower alkylcyclopentane-1,3-dione and ethyl acrylate to yield ethyl β-(1'-lower alkyl-2', 5'-dioxocyclopentyl)propionate. The 2-oxo group is then modified, if desired, using conventional procedures such as forming the corresponding ethylenedioxy or forming the corresponding hydroxyl by reduction and then esterification or etherification and thereafter hydrolysis and cyclization is performed. The tricyclic enol lactones of formula I can be similarly prepared using the method of Netherlands Pat. No. 6,414,702 (1965).

What is claimed is:
1. A compound of the formula

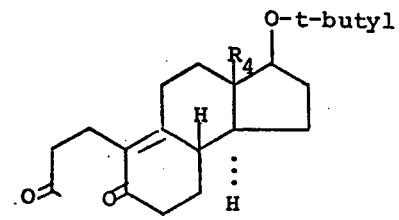

wherein $R_4$ is lower alkyl having from 1 to 6 carbon atoms.

* * * * *